United States Patent [19]

Fujishiro et al.

[11] 4,033,169
[45] July 5, 1977

[54] HYDROCARBON CONCENTRATION SENSOR FOR USE IN ENGINE EXHAUST GAS

[75] Inventors: Takeshi Fujishiro, Yokohama; Naomasa Sunano, Fukuchiyama, both of Japan

[73] Assignees: Nissan Motor Co., Ltd., Yokohama; Shinyei Kaisha, Kobe, both of Japan

[22] Filed: Aug. 7, 1975

[21] Appl. No.: 602,891

[30] Foreign Application Priority Data

Aug. 9, 1974  Japan ............... 49-91246

[52] U.S. Cl. .................. 73/23; 23/254 E; 338/34
[51] Int. Cl.[2] .................. G01N 27/12
[58] Field of Search ............ 73/23, 27 R; 324/65 R, 324/65 P, 71 SN; 338/34, 35; 340/237 R; 23/252 E, 232 R, 254 E, 254 R

[56] References Cited
UNITED STATES PATENTS

| | | | |
|---|---|---|---|
| 2,768,069 | 10/1956 | Thompson | 73/27 R |
| 3,200,011 | 8/1965 | Baker | 73/27 R |
| 3,586,486 | 6/1971 | Kim et al. | 73/27 R |
| 3,610,023 | 10/1971 | Ageikin et al. | 73/23 |
| 3,687,631 | 8/1972 | Zegel | 73/27 R |
| 3,695,848 | 10/1972 | Taguchi | 73/27 R |
| 3,699,803 | 10/1972 | Sumi et al. | 73/27 R |
| 3,751,968 | 8/1973 | Loh et al. | 73/23 |
| 3,864,628 | 2/1975 | Klass et al. | 73/23 |

Primary Examiner—Richard C. Queisser
Assistant Examiner—Stephen A. Kreitman

[57] ABSTRACT

A sensor having an $n$-type oxide semiconductor layer and a $p$-type oxide semiconductor layer spaced from and electrically connected in series with each other and two fixed resistors connected in series with each other, wherein the two semiconductor layers and two resistors are connected to construct a four-arm bridge.

8 Claims, 5 Drawing Figures

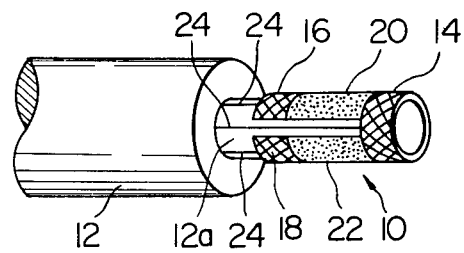
Fig. 1
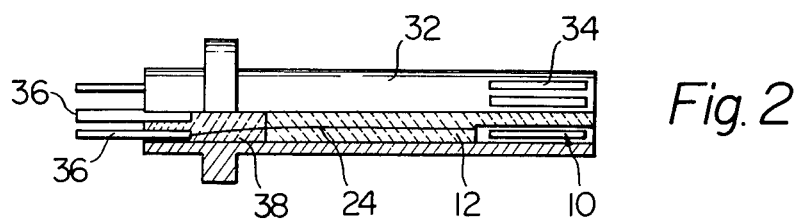
Fig. 2
Fig. 3
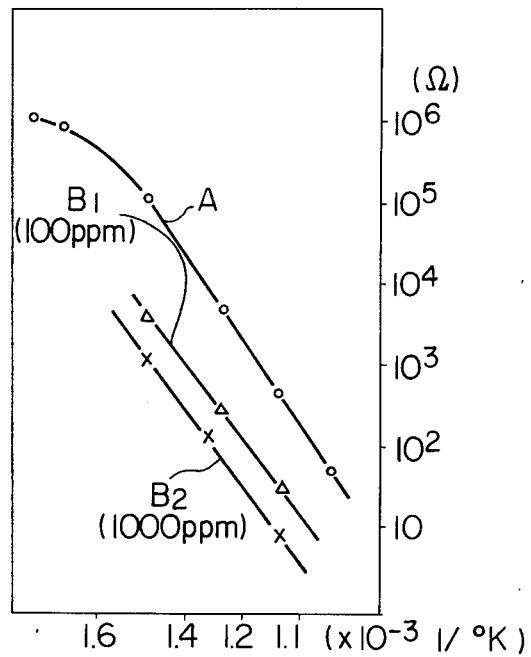

HYDROCARBON CONCENTRATION SENSOR FOR USE IN ENGINE EXHAUST GAS

This invention relates to a sensor of the oxide semiconductor type for the measurement of concentrations of hydrocarbons in a gaseous mixture such as exhaust gas from an internal combustion engine.

In the art of reducing air pollution attributable to automobile internal combustion engines, catalytic conversion of harmful components of the exhaust gas into harmless gases has been accepted as a quite effective method particularly for reducing the concentrations of carbon monoxide (CO) and unburned hydrocarbons (HC). When a catalytic converter is installed in the exhaust line of the engine, it is important to prevent the temperature in the converter from increasing extraordinarily since the catalyst in the converter will be damaged and lose its catalytic property when exposed to excessively high temperatures. In practice, a main cause for an extraordinary temperature rise in the converter is occurrence of misfires in the engine.

A total concentration of HC in the exhaust gas is usually below 2500 ppm when the exhaust gas flows into the converter under normal engine operation conditions, but easily multiplies by a factor of 2 to 10 or larger on the occurrence of misfires. Such increased concentrations of HC result in evolution of an increased quantity of reaction heat in the converter. The occurrence of misfires, therefore, can be detected by detecting changes in the concentrations of HC in the exhaust gas. When changes in the concentrations are measured with a sensor which produces an electrical signal correlated to the concentrations, the signal is supplied to an alarm apparatus which gives the driver a warning of the engine not working properly and/or the catalyst being overheated in response to a change in the level or mode of the signal. The signal may alternatively be supplied to a control system for controlling the feed rate of the exhaust gas to the catalytic converter by, for example, allowing a portion of the exhaust gas to bypass the converter temporarily when overheating of the catalyst is feared.

As is known, an oxide semiconductor the electronic conductivity of which varies by exposure to a reducing gas is useful as an essential element of the above described type of sensor since HC in the exhaust gas includes reducing compounds as exemplified by isobutane and toluene.

Conventional HC sensors for use in the exhaust lines of automobile internal combustion engines utilize, so far as we know, a sintered element of an $n$-type oxide semiconductor containing $SnO_2$ as its principal component. Changes in the electronic conductivity of this element with variations in the HC concentrations in the exhaust gas are considered to be attributable to the changes in the surface conductivity of the semiconductor element caused by absorption of HC on the surface of the element. When this element is exposed to an actual exhaust gas, however, the variations over a very wide range in the exhaust gas temperature disturb measurement of HC concentrations with this sensor since variations in the bulk conductivity of the element with variations in the gas temperature surpasses the variations in the surface conductivity in magnitudes. In the installation of such a sensor in the exhaust line, it is usually required that the sensor be located close to, or at a distance less than 1 m from the exhaust manifold taking into account the responsiveness of an alarm apparatus or a flow control system to the signal produced by the sensor. The exhaust gas temperature at such a distance from the exhaust manifold ranges usually from about 400° to about 800° C and varies continually over a wide range. The sensor of the described type, on the other hand, cannot exhibit a satisfactorily sharp responsiveness to the variations in the concentrations of HC when the ambient temperature is continually above about 300° C.

It is an object of the present invention to provide a sensor for sensing changes in the concentrations of unburned hydrocarbons (HC) in exhaust gas discharged from an internal combustion engine, which sensor responds sensitively and exactly to changes in the concentrations of HC even when the temperature of the exhaust gas to which the sensor is exposed varies continually and significantly over a range between about 300° and about 800° C.

According to the present invention, a sensor for sensing changes in the concentrations of unburned hydrocarbons (HC) in exhaust gas discharged from an internal combustion engine comprises a support member of a dielectric and heat-resistant material, a first layer of an $n$-type oxide semiconductor formed locally on the surface of the support member, the conductivity of which semiconductor increases as the concentrations of HC in the ambient atmosphere increase, and a second layer of a $p$-type oxide semiconductor formed on the surface of the support member locally and spaced from the first layer, the conductivity of which semiconductor decreases as the concentrations of HC in the ambient atmosphere increase. The sensor further comprises a first electrode in contact with both the first and second layers, a second electrode in contact with the first layer but spaced from the first electrode, a third electrode in contact with the second layer but spaced from the first and second electrodes, and two resistors connected in series with each other. In this sensor, the two semiconductor layers and two resistors are electrically connected to construct a four-arm bridge circuit.

The $n$-type oxide semiconductor for use in a sensor according to the invention is a sintered mixture of at least three oxides, namely, ZnO or $SnO_2$, $V_2O_5$ or $Sb_2O_3$, and one selected from $Al_2O_3$, $SiO_2$, $Cu_2O$, $Ag_2O$, PbO and $Nd_2O_3$. The p-type oxide semiconductor is a sintered ternary oxide containing $La$ or $Sm$; $Mg$, $Ca$, $Sr$, or $Zr$; and $Cr$, $Co$ or $Ni$.

Other features and advantages of the invention will become apparent from the following detailed description of preferred embodiments thereof with reference to the accompanying drawings, in which:

FIG. 1 is a perspective view of a sensing part of a sensor according to the invention;

FIG. 2 is a side view, partly in section, of the same part covered with a protective member;

FIG. 3 is a graph showing the conductivity characteristics of an $n$-type semiconductor used in the sensor of FIG. 1 as a sensing element;

Figure 4:
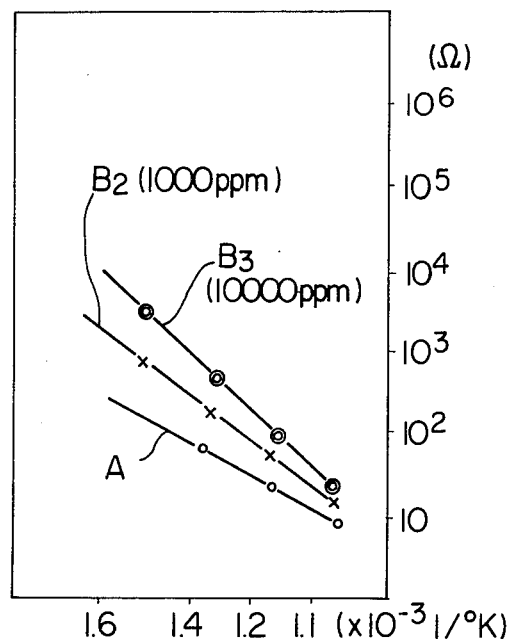
FIG. 4 is a similar graph for a $p$-type semiconductor used as another sensing element of the same sensor.

Referring at first to FIG. 1, a sensing part 10 of a sensor according to the invention is formed on the outer surface of a support member 12 which is cylindrical in this example and stepped to have a small diameter end portion 12a. The support member 12 is made of a heat-resistant and electrically non-conductive, or dielectric material as exemplified by alumina ceramics. Three electrodes 14, 16 and 18 are formed on the surface of the small diameter end portion 12a fixedly and separately from each other. These electrodes 14, 16 and 18 are made of a corrosion and heat-resistant material and preferably formed by applying a paste comprising a finely powdered platinum, gold or palladium onto the surface of the end portion 12a followed by heating to fuse the metal and remove the liquid component of the paste. A first semiconductor layer 20 is formed on the surface of the end portion 12a so as to fill the gap between the first and second electrodes 14 and 16. This electrode layer 20 is electrically connected with both the first and second electrodes 14 and 16 but isolated from the third electrode 18. Similarly, a second semiconductor layer 22 is formed close to but separately from the first layer 20. The second layer 22 is electrically connected with both the first and third electrodes 14 and 18 but isolated from the second electrode 16. Each of these electrode 14, 16 and 18 is connected to a lead 24.

The first and second semiconductor layers 20 and 22 are made of two different types of oxide semiconductors, respectively. The first layer 20 is of an $n$-type oxide semiconductor which is characterized by increase in its conductivity with increase in the concentration of a reducing substance in the ambient atmosphere. The second layer 22 is of a $p$-type oxide semiconductor which exhibits decrease in its conductivity with increase in the same concentration. As to the dependence on the temperature, both types of oxide semiconductors exhibit increase in the conductivity with increase in the temperature. A total concentration of HC in an engine exhaust gas can be detected by either of these $n$-type and $p$-type oxide semiconductors since the proportions of effectively reducing compounds to the whole HC remain almost unchanged with changes in the total concentration of HC in the exhaust gas.

According to the invention, two specific oxide compositions are used as the $n$-type and $p$-type semiconductors for the semiconductor layers 20 and 22, respectively, to attain sharp responsiveness to the variations in the HC concentrations in the exhaust gas even at elevated temperatures ranging from about 300° to about 800° C at the narrowest. A sintered oxide mixture consisting of 3 to 5 oxides selected from $SnO_2$, $ZnO$, $Sb_2O_3$, $V_2O_5$, $Al_2O_3$, $Cu_2O$, $SiO_2$, $Ag_2O$ and $Nd_2O_3$ is used as an n-type semiconductor. A catalytic amount of $Mn$, $Pt$ and/or $Pd$ may be added to the oxide mixture. The p-type semiconductor is a sintered ternary oxide containing $La$, or $Sm$; $Mg$, $Ca$, $Sr$ or $Zr$; and $Cr$, $Co$ or $Ni$. A catalytic amount of $Pt$ and/or $Pd$ may be added to the ternary oxide.

Preferred examples of the n-type oxide semiconductors are as follows.

ZnO(85–93% by weight):$V_2O_5$(7–12%):$Ag_2O$(0.5–3%)
ZnO(85–93%):$V_2O_5$(7–12%):PbO(0.5–3%)
$SnO_2$(95–99%):$Sb_2O_3$(0.5–4%):$Al_2O_3$(0.05–3%)
$SnO_2$(85–93%):$Sb_2O_3$(3–7%):$SiO_2$(0.5–8%)
$SnO_2$(85–93%):$Sb_2O_3$(3–7%):$Nd_2O_3$(0.5–8%)
$SnO_2$(85–93%):$Sb_2O_3$(3–7%):$Cu_2O$(0.5–8%)

At least one of $Mn$, $Pt$ and $Pd$ may be added to any of the above compositions in an amount of 0.1 to 10% by weight of the oxide mixture as a catalyst.

Preferred examples of the $p$-type oxide semiconductors are represented by the following formulas.

$La_{1-x}Ca_xCrO_{3-y}$
$La_{1-x}Zr_xCrO_{3-y}$
$La_{1-x}Mg_xNiO_{3-y}$
$Sm_{1-x}Sr_xCoO_{3-y}$ where $x$ ranges from 0.1 to 0.8, and $y$ takes a value from 0 to 0.1 depending on the sintering conditions. $Pt$ and/or $Pd$ may be added to any of these ternary oxides in an amount of 0.1 to 2% by weight of the ternary oxide.

These $n$-type and $p$-type oxide semiconductors exhibit changes in the conductivity when exposed to an alcohol or carbon monoxide other than reducing hydrocarbons.

The semiconductor layer 20 is formed by applying a paste containing a mixture of finely powdered oxides as described onto the surface of the end portion 12a of the support member 12 followed by sintering in air at a temperature of 1000° to 1100° C. The second semiconductor layer 22 is formed generally in the same manner except that $La$ and $Ca$ are contained in the paste in the form of $La(OH)_3$ and $CaCO_3$, respectively, and that the sintering temperature ranges from 1300° to 1600° C. Both the first and second layers 20 and 22 may be coated with a thin and gas permeable layer of $Al_2O_3$ for the protection of the semiconductors against physical damages and absorption of water vapor. Such a protective coating can be formed generally similarly to the semiconductor layers 20 and 22 by the use of a paste containing powdered $Al_2O_3$.

The dependences of the resistance of the $n$-type oxide semiconductor layer 20 between the first and second electrodes 14 and 16 on both the temperature and a total concentration of HC in the ambient atmosphere are shown in the graph of FIG. 3 with a composition, $SnO_2$:$Sb_2O_3$:$SiO_2$(96:3.5:0.5) added with $Pd$(0.5%). The curve A represents the resistance changes in clean air, and curves $B_1$ and $B_2$ the changes in two differently composed exhaust gases, respectively. FIG. 4 is a similar graph for the $p$-type oxide semiconductor layer 22 with a composition represented by $La_{0.8}Ca_{0.2}CrO_3$ added with $Pd$(1%) except that the curve $B_3$ represents the resistivity change in another differently composed exhaust gas.

Figure 5:
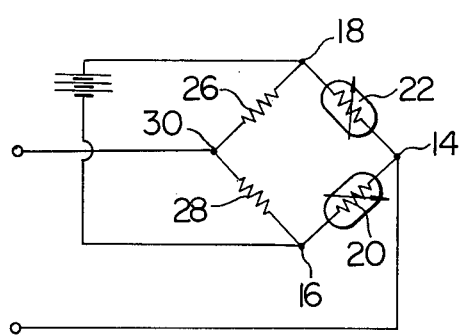
FIG. 5 is a circuit diagram of a sensor of the invention.

It is an important feature of a sensor according to the invention that the sensing part 10 has the $n$-type oxide semiconductor layer 20 and the $p$-type oxide semiconductor layer 22 connected electrically in series with each other in preparation for constructing a bridge circuit as shown in FIG. 5. A well known four-arm bridge is constructed by providing an electrical connection between the second and third electrodes 16 and 18 through a circuit consisting of two fixed resistors 26 and 28 in series connection with an intermediate junction point 30. Due to the reversely tending changes in the resistances of the $n$-type and $p$-type semiconductor layers 20 and 22 with a change in the total concentration of HC in the exhaust gas, a sensor of the invention is far more sensitive than a conventional sensor having an $n$-type semiconductor alone. Furthermore, the resistors 26 and 28 accomplish compensation for thermal variations of the resistivities of the semi-conductors 20 and 22 when the resistors 26 and 28 also are arranged so as to be exposed to the exhaust gas.

When a sensor of the invention is installed in the exhaust line of an automobile engine between the exhaust manifold and a catalytic converter, misfires in the engine can be detected quickly due to a sharp and exact responsiveness of the sensor to changes in the total concentration of HC. Accordingly, some preventive measures can be taken against possible damage or destruction by overheating of the catalyst in the converter.

A sensor according to the invention may be constructed in any fashion as a whole, or similarly to conventional gas concentration sensors. The support member 12 for the sensing part 10 is preferably enclosed fixedly in a protective tube 32 of, e.g., stainless steel as shown in FIG. 2. The sensing part 10 is covered with this tube 32 forming an annular space therebetween. The tube 32 has a plurality of axially elongate louvers 34 formed in its peripheral wall at an end region covering the sensing part 10. The leads 24 extend to the other end of the tube 32 through axial holes formed in the support member 12 and are connected to terminals 36 which are fixed to the tube 32. The terminal side end section of the tube 32 is preferably filled with an insulating and heat-resistant filler 38 such as an alumina cement. The resistors 26 and 28 may be installed in the same tube 32, or may alternatively be supported by a separate member.

What is claimed is:

1. A sensor for sensing changes in the concentrations of unburned hydrocarbons in exhaust gas discharged from an internal combustion engine, comprising:
   a support member of a dielectric and heat-resistant material;
   a first layer of an $n$-type oxide semiconductor formed locally on a surface of said support member, the conductivity of said semiconductor increasing as the concentrations of the unburned hydrocarbons in the ambient atmosphere increase;
   a second layer of a $p$-type oxide semiconductor formed on said surface of said support member locally and spaced from said first layer, the conductivity of said $p$-type oxide semiconductor decreasing as the concentrations of the unburned hydrocarbons increase; both said first and second semiconductors having negative temperature coefficients of resistivity;
   a first electrode arranged in contact with both of said first and second layers;
   a second electrode arranged in contact with said first layer and spaced from said first electrode;
   a third electrode arranged in contact with said second layer and spaced from both of said first and second electrodes; and
   two resistors connected in series with each other; said first and second layers and said two resistors being electrically connected to construct a four-arm bridge.

2. A sensor for sensing changes in the concentrations of unburned hydrocarbons in exhaust gas discharged from an internal combustion engine, comprising:
   a support member of a dielectric and heat-resistant material;
   a first layer of an $n$-type oxide semiconductor formed locally on a surface of said support member, the conductivity of said semi-conductor increasing as the concentrations of the unburned hydrocarbons in the ambient atmosphere increase, wherein said $n$-type oxide semiconductor is a sintered mixture of three oxides, the first being selected from the group consisting of ZnO and $snO_2$, the second being selected from the group consisting of $V_2O_5$ and $Sb_2O_3$, the third being selected from the group consisting of $Al_2O_3$, $SiO_2$, $Cu_2O$, $Ag_2O$, PbO and $Nd_2O_3$;
   a second layer of a $p$-type oxide semiconductor formed on said surface of said support member locally and spaced from said first layer, the conductivity of said $p$-type oxide semiconductor decreasing as the concentrations of the unburned hydrocarbons increase, wherein said $p$-type oxide semiconductor is a sintered ternary oxide containing a first element selected from the group consisting of La and Sm, a second element selected from the group consisting of Mg, Ca, Sr and Zr, and a third element selected from the group consisting of Cr, Ni and Co;
   both said first and second layers being so arranged as to be exposed to the exhaust gas;
   a first electrode arranged in contact with both of said first and second layers;
   a second electrode arranged in contact with said first layer and spaced from said first electrode;
   a third electrode arranged in contact with said second layer and spaced from both of said first and second electrodes; and
   two resistors connected in series with each other; said first and second layers and said two resistors being electrically connected to construct a four-arm bridge.

3. A sensor as claimed in claim 2, wherein the amounts of the first, second and third oxides of said $n$-type oxide semiconductor are 85 to 99%, 0.5 to 12% and 0.05 to 8% by weight, respectively.

4. A sensor as claimed in claim 3, wherein said $n$-type oxide semiconductor further comprises at least one catalytic metal selected from the group consisting of Mn, Pt and Pd in an amount of 0.1 to 10% by weight of said mixture.

5. A sensor as claimed in claim 2, wherein said $p$-type oxide semiconductor is represented by the formula $$M_{1-x}M'_xM''O_{3-y}$$

where M, M' and M" represent said first, second and third elements, respectively, $x$ ranges from 0.1 to 0.8, and $y$ ranges from 0 to 0.1.

6. A sensor as claimed in claim 5, wherein said $p$-type oxide semiconductor further comprises at least one catalytic metal selected from the group consisting of Pt and Pd in an amount of 0.1 to 2% by weight of said ternary oxide.

7. A sensor as claimed in claim 2, wherein said support member has a cylindrical portion, said first and second layers being formed on the outer peripheral surface of said cylindrical portion generally symmetrically with respect to the longitudinal axis of said cylindrical portion, said first, second and third electrodes being formed on said outer peripheral surface, said first electrode having a circular cross section, said second and third electrodes being arranged generally symmetrically with respect to said axis at distances equal to axial lengths of said first and second layers, respectively, from said first electrode.

8. A sensor as claimed in claim 2, further comprising a porous layer of $Al_2O_3$ formed on said first and second layers.

* * * * *